United States Patent [19]

Castor et al.

[11] Patent Number: 5,854,064
[45] Date of Patent: Dec. 29, 1998

[54] METHODS FOR FRACTIONATION OF BIOLOGICALLY-DERIVED MATERIALS

[75] Inventors: Trevor P. Castor, Arlington; Hemant M. Chikarmane, Reading; Glenn T. Hong, Westborough; Christopher Shallice, Southborough, all of Mass.

[73] Assignee: Aphios Corporation, Woburn, Mass.

[21] Appl. No.: 690,626

[22] Filed: Jul. 31, 1996

[51] Int. Cl.⁶ .............................. C12C 1/00; C07B 17/00
[52] U.S. Cl. ....................... 435/308.1; 435/267; 435/814; 435/816
[58] Field of Search ................................ 435/267, 308.1, 435/814, 816

[56] References Cited

U.S. PATENT DOCUMENTS 5,380,826  1/1995  Castor et al. ........................... 530/422
5,440,055  8/1995  Castor ..................................... 549/510

OTHER PUBLICATIONS

Sanger et al. "A Rapid Super . . . Critical Fluid . . . ", 96th Gen'l Meeting of the ASM; 96(0) 1996.336, 1996.

Patzig et al. "Infrared Spectrometry" Analytical Chem., 1992, 64(12), 270–302.

*Primary Examiner*—Francisco Prats
*Assistant Examiner*—Deborah K. Ware

[57] ABSTRACT

Supercritical and near critical fluids are used to fractionate biomass materials in two steps. In the first step, the biomass is exposed to elevated pressure supercritical or near critical fluid to bring about disruption of the biomass. In the second step, the disrupted biomass is subjected to a multiplicity of supercritical or near critical fluid extraction steps, with different solvation conditions used for each fraction. Thus, fractionation of the biomass is effected.

8 Claims, 1 Drawing Sheet

METHODS FOR FRACTIONATION OF BIOLOGICALLY-DERIVED MATERIALS

FIELD OF THE INVENTION

This invention relates to methods for extracting fractions from material of biological origin. The fractions potentially contain one or more compounds which exhibit biological activity. The methods feature supercritical and near critical fluids.

BACKGROUND OF THE INVENTION

At the present time, a number of major pharmaceutical companies are actively carrying out programs for the discovery of drugs from natural products. Typically, such programs involve screening of a large number of natural materials for therapeutic or other biological activity. These biomass materials may be obtained or derived from plant, animal, or microbial sources. Screening is carried out by assaying samples for indications of, for example, cytotoxicity, antibacterial activity, or antiviral activity.

In preparation for screening, the biomass is typically exposed to an extraction step. In many cases, however, the bioactive materials of interest may be sequestered within the substrate and not accessible to extraction. Thus, depending upon the particular biomass, the extraction may be facilitated by a preliminary size reduction (comminution) or disruption step. Comminution/disruption methods include for example grinding, sonication, and homogenization. Conventional comminution/disruption methods may have the disadvantages of incomplete disruption and/or product deterioration. They may also be time-consuming and expensive.

For the extraction, the biomass is contacted with a solvent such as butanol or ethyl acetate, so that compounds of potential interest may migrate from the biomass substrate to the solvent phase. Sometimes multiple extraction steps may be carried out on a single batch of biomass. A "fraction" refers to the material recovered from the biomass in a single one of these extraction steps. Fractions from the extraction steps are further processed so that they may be assayed for the activity of interest. Because different extraction methods will produce different extract profiles, there is a continuing interest in the development of new extraction techniques.

Conventional solvents are not always ideal for biomass extractions. These solvents can be difficult to remove from the compounds potentially exhibiting bioactivity, and also may extract a mixture of compounds which can mask bioactivity in an assay. The solvents may not penetrate membranes or other cellular structures surviving disruption. The solvation properties of conventional solvents cannot be readily modified by changing temperature, pressure, or the concentration of modifying cosolvents, and thus may be cumbersome to use when it is desired to carry out certain types of fractionations such as the selective extraction of compounds of varying polarity.

It would be highly desirable to have a method for fractional extraction of biomass constituents, including those which are sequestered within cells. It would be highly desirable to have a solvent system which can be readily modified by physical parameters and the addition of modifying cosolvents to selectively extract compounds of varying polarity, volatility, or hydrophilicity. It would be highly desirable to have a physical-chemical disruption process that provides for a high level of disruption without loss of active material. It would be desirable to disrupt biomass and form one or more fractions using a single apparatus.

SUMMARY OF THE INVENTION

Aspects of the present invention employ materials known as supercritical fluids. A material becomes a supercritical fluid at conditions which equal or exceed both its critical temperature and critical pressure. These parameters are intrinsic thermodynamic properties of all sufficiently stable pure compounds and mixtures. Carbon dioxide, for example, becomes a supercritical fluid at conditions which equal or exceed its critical temperature of 31.1° C. and its critical pressure of 72.8 atm (1,070 psig). In the supercritical fluid region, normally gaseous substances such as carbon dioxide become dense phase fluids which have been observed to exhibit greatly enhanced solvating power. At a pressure of 3,000 psig (204 atm) and a temperature of 40° C., carbon dioxide has a density of approximately 0.8 g/cc and behaves much like a nonpolar organic solvent, having a dipole moment of zero debyes. A supercritical fluid uniquely displays a wide spectrum of solvation power as its density is strongly dependent upon temperature and pressure. Temperature changes of tens of degrees or pressure changes by tens of atmospheres can change a compound's solubility in a supercritical fluid by an order of magnitude or more. This unique feature allows for the fine-tuning of solvation power and the fractionation of mixed solutes. The selectivity of nonpolar supercritical fluid solvents can also be enhanced by addition of compounds known as modifiers (also referred to as entrainers or cosolvents). These modifiers are typically somewhat polar organic solvents such as acetone, ethanol, methanol, methylene chloride or ethyl acetate. Varying the proportion of modifier allows a wide latitude in the variation of solvent power.

In addition to their unique solubilization characteristics, supercritical fluids possess other physicochemical properties which add to their attractiveness as solvents. They can exhibit liquid-like density yet still retain gas-like properties of high diffusivity and low viscosity. The latter increases mass transfer rates, significantly reducing processing times. Additionally, the ultra-low surface tension of supercritical fluids allows facile penetration into microporous materials, increasing extraction efficiency and overall yields.

While similar in many ways to conventional nonpolar solvents such as hexane, it is well-known that critical fluid solvents can extract a different spectrum of materials than conventional techniques. Product volatilization and oxidation as well as processing time and organic solvent usage can be significantly reduced with the use of supercritical fluid solvents.

A material which is somewhat below its critical conditions will have properties which are similar to those of the substance in the supercritical fluid state. These so-called "near critical" fluids are also useful for the practice of this invention. For the purposes of this invention, a near critical fluid is defined as a fluid which is at a temperature between its critical temperature ($T_c$) and 75% of its critical temperature, and at a pressure between its critical pressure ($P_c$) and 75% of its critical pressure. In this definition, pressure and temperature are defined on absolute scales, e.g., Kelvins and psia. Table 1 shows how these requirements relate to some of the fluids relevant to this invention. To simplify the terminology, materials which are utilized under conditions which are supercritical, near critical, or exactly at their critical point will jointly be referred to as "critical" fluids.

TABLE 1

Physical properties of critical fluid solvents.

| Fluid | Formula | BP, °C. | $P_{vap}$, psia @ 25° C. | Tc, °C. | Pc, psia | 0.75 Tc, °C. | 0.75 Pc, psia |
|---|---|---|---|---|---|---|---|
| Carbon dioxide | $CO_2$ | −78.5 | 860 | 31.1 | 1070 | −45.0 | 803 |
| Nitrous oxide | $N_2O$ | −88.5 | 700 | 36.5 | 1051 | −41.0 | 788 |
| Propane | $C_3H_8$ | −42.1 | 130 | 96.7 | 616 | 4.2 | 462 |
| Ethane | $C_2H_6$ | −88.7 | 570 | 32.3 | 709 | −44.1 | 531 |
| Ethylene | $C_2H_4$ | −103.8 | NA | 9.3 | 731 | −61.4 | 548 |
| Freon 11 | $CCl_3F$ | 23.8 | 15 | 198.1 | 639 | 80.3 | 480 |
| Freon 21 | $CHCl_2F$ | 8.9 | 24 | 178.5 | 750 | 65.6 | 562 |
| Freon 22 | $CHClF_2$ | −40.8 | 140 | 96.1 | 722 | 3.8 | 541 |
| Freon 23 | $CHF_3$ | −82.2 | 630 | 26.1 | 700 | −48.7 | 525 |

Table 1 Notes:
BP = Normal boiling point;
$P_{vap}$ = Vapor pressure

The present invention utilizes critical fluids to fractionate cellular biomass materials in two steps. In the first step, the biomass is disrupted by exposure to the critical fluid. It is hypothesized that this disruption involves at least two mechanisms, the first being liberation of cell envelope constituents to cause cell envelope permeability. The cell envelope constituents are not necessarily solvated in the critical fluid, i.e., they may remain in the phase containing the biomass, but in any case lose their structural association with the cell. The resulting permeability of the cell envelope makes certain contents of the cell accessible to be extracted in subsequent steps. The second mechanism of disruption involves an explosive phenomenon due to the expanding critical fluid upon depressurization of the biomass. In the latter case, rapid decompression is sometimes desirable. Larger systems may require longer to decompress than smaller systems. In the former case, decompression is not required to provide the desired disruption. The nature of the biomass determines the relative importance of the two disruption mechanisms in any given application. During this first disruption step, an extract fraction may optionally be collected from the critical fluid contacting the biomass. In the second step of the fractionation, the disrupted biomass is subjected to a multiplicity of critical fluid extraction steps, the steps being characterized in that different solvation conditions are used in each. Thus, fractionation of the biomass is effected. As mentioned, critical fluid solvation properties may be varied by adjusting pressure, temperature, or modifier concentration. These parameters may be adjusted individually or in combination. Solvation conditions may also be varied through the use of different modifiers in a single fractionation procedure, although this would not typically be advantageous.

Preferably, each subsequent critical fluid is altered to change the solvation properties of the extracting fluid, so that each step can recover a different spectrum of compounds. The solvation properties of critical fluids can be altered by changing the temperature or pressure of the fluid. By way of example, a preferred temperature and pressure for a critical fluid comprising carbon dioxide is a temperature in the range of 10° to 60° C. and a pressure in the range of 2000 to 4000 psig.

Preferred critical fluids comprise carbon dioxide, nitrous oxide, ethylene, ethane, propane and freons. The fluid may also contain modifiers. Preferred modifiers are methanol, ethanol, propanol, butanol, methylene chloride, ethyl acetate and acetone.

A preferred modifier comprises methanol. In one preferred embodiment, each subsequent extraction employs a larger concentration of methanol. Thus, the plurality of critical fluids becomes increasingly more hydrophilic. The first extraction step tends to remove lipophilic compounds while the last extraction step tends to remove hydrophilic compounds. Removal of the lipophilic materials allows the next more hydrophilic critical fluid to have access to more hydrophilic compounds trapped in cellular structures. Preferred methanol concentration ranges for a first extraction step on disrupted biomass, based on carbon dioxide at a pressure of 3000 psig and a temperature of 40° C., are 0–5 volume %. For the same temperature and pressure, 5–10 volume % methanol is preferred for a second extraction step; 10–20 volume % methanol is preferred for a third extraction step; 20–30 volume % methanol is preferred for a fourth extraction step; 30–50 volume % methanol is preferred for a fifth extraction step.

Surprisingly and unexpectedly, the combination of disruption and extraction with critical fluids produces larger numbers of fractions exhibiting biological activity than corresponding fractions derived from conventional organic solvent extractions. The use of critical fluids allows for easy removal of much of the solvent by mere depressurization. Use of a single apparatus to perform both the disruption and extraction steps minimizes labor and increases efficiency. Indeed, the entire process can be readily automated. The use of critical fluids allows the extraction conditions to be readily varied by temperature, pressure, or modifier solvents. Use of critical fluids for both the disruption and extraction simplifies the procedure and minimizes equipment needs, processing time, potential for contamination, and loss of yield. These and other features and advantages will be readily apparent from the drawing and detailed discussion which follow.

DETAILED DESCRIPTION OF PREFERRED EMBODIMENTS

Figure 1:
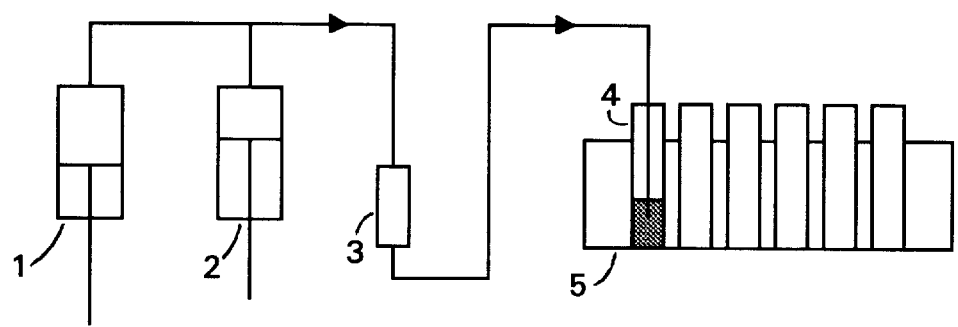
FIG. 1 shows a flow scheme for the extraction apparatus used in the examples of this specification.

The present invention has been practiced in the area of screening microbes for novel therapeutically active compounds. Microorganisms were cultured from natural sources including, but not limited to, soil, air, water, swamps, hot springs, sea water, animal or plant surfaces and parts. Depending on the source of the microorganism, specific media were used for isolations. Typical isolation media were nutrient agar (Difco), tryp-soy agar (Difco), and Sabouraud's dextrose agar (Difco) for terrestrial organisms, and lean nutrient agar, 2216 marine agar (Difco), and chitin sea water agar for marine microorganisms. Soil or other samples were diluted in sterile physiological saline or sea water, and about 100 μl of the dilution was spread uniformly on the surface of the agar. Incubation temperatures were dependent on the optimum temperature, ranging from 15° C. to 80° C., but were typically 25° C. Plates were incubated for up to three weeks, and colonies were picked with a sterile inoculating needle and transferred to fresh plates and slants. After checking for their ability to grow in fermentation media such as those described below, 10% glycerol was added to the cultures, which were quick frozen by immersion in liquid nitrogen. The glycerol stocks were maintained at −80° C.

Stock organisms were scraped from glycerol stocks using a sterile wooden applicator stick, and streaked out on agar plates. Terrestrial isolates were typically streaked out on Tryp-soy agar (Difco) prepared in deionized water. Marine isolates were streaked on Tryp-soy agar (Difco) made in an artificial sea water base. We have used the GP2 sea water composition (Bidwell, J. P., and Spotte, S. *Artificial Seawaters. Formulas and Methods.* Jones and Bartlett, Boston, 1985), which is as follows:

| GP2 sea water (per liter) | | | |
|---|---|---|---|
| NaCl | 23.9 g | $Na_2SO_4$ | 4 g |
| KCl | 0.698 g | $NaHCO_3$ | 0.193 g |
| KBr | 0.1 g | $Na_2B_4O_7.10H_2O$ | 0.039 g |
| $MgCl_2.6H_2O$ | 0.108 g | $CaCl_2.2H_2O$ | 1.5 g |
| $SrCl_2.6H_2O$ | 0.0243 g | $NaH_2PO_4.H_2O$ | 0.0128 g |
| Ferric citrate. $H_2O$ | $2.42 \times 10^{-5}$ g | $Na_2MoO_4.2H_2O$ | $8.3 \times 10^{-5}$ g |
| KI | $2.18 \times 10^{-5}$ g | $ZnSO_4.7H_2O$ | $2.18 \times 10^{-5}$ g |
| $NaVO_3$ | $6.1 \times 10^{-6}$ g | $MnSO_4.H_2O$ | $6.08 \times 10^{-7}$ g |
| Urea | $4.47 \times 10^{-2}$ g | Thiamine.HCl | $1.95 \times 10^{-3}$ g |
| Biotin | $9.99 \times 10^{-7}$ g | Cyanocobalamine | $9.77 \times 10^{-7}$ g |

Cultures for routine use were maintained on the appropriate agar slants or plates kept at 4° C. Cultures were routinely examined by colony characteristics, Gram-staining, and cell morphology, to ensure axenicity.

Four liquid fermentation media differing in chemical composition were used to grow any given culture. Use of more than one medium helps to maximize the diversity of secondary metabolites. The media described below are high or low in particular nutrients, specifically carbon and nitrogen. Carbon sources were glucose, glycerol, or Na acetate. Nitrogen sources were peptone, yeast extract, and beef extract. For terrestrial organisms, the media were prepared in deionized water. Marine fermentation media were prepared in GP2 sea water. Fermentations were carried out in 500 ml Erlenmeyer flasks. Each flask contained 100–125 ml of the appropriate medium, and was sterilized by autoclaving at 121° C. and 1.1 kPa for 15 min.

Each culture was inoculated into four media such as those described above. A sterile inoculating loop or wooden applicator stick was utilized to transfer a loopful of the culture from the plate to the flask. The flasks were shaken under controlled conditions. The incubation temperature of 25° C. was sufficient to support growth of the majority of the microorganisms. The ratio of the medium volume to that of the flask (1:5), accompanied by constant shaking at 250 rpm (2.5 cm stroke), was sufficient to maintain adequate oxygen levels during the growth period. The 7 day incubation period ensured that all of the cultures would reach the stationary phase of growth, where most of the secondary metabolite production is expected to take place. Before harvesting, cultures were examined microscopically by staining to confirm their axenic nature.

Organic solvent extraction was carried out using conventional methods, with solvents such as butanol or ethyl acetate. Typically, 1 vol of the grown culture was extracted by adding 0.5 vol butanol to the flask. The flasks were shaken at 250 rpm for 30 min, and were then allowed to stand for 30 min. Most of the lower aqueous layer was suctioned off with a 1 ml plastic pipet attached to a vacuum pump. The flask contents were transferred to centrifuge tubes, which were centrifuged in a Sorvall RC2-B centrifuge at 8000 g for 10 min, to completely separate the phases. The upper butanol phase was collected by aspiration using a disposable Pasteur pipet, and transferred to a 15 ml polypropylene storage tube.

Critical fluid extractions were carried out on an ISCO (Lincoln, Nebraska) SFX 3560 automated extractor. As shown in FIG. 1, this is a dual pump system, utilizing syringe pump 1 for neat critical fluid and syringe pump 2 for modifier. The pumps are independently controllable, allowing easy adjustment of the fluid composition. To prepare a sample, the culture was centrifuged at 8000 g for 10 min. The cell pellet was collected after decanting the supernatant, transferred to a polystyrene weighing dish, and dried at 25°–37° C. for 1 day, with or without vacuum. The dried cell pellet was transferred to a 10 ml ISCO extraction cartridge, numbered 3 in the figure, after which the cartridge was filled with 3 mm diameter glass beads to reduce the dead volume. After loading a cartridge on the cartridge holder, the disruption/extraction procedure was commenced. The system was brought to 3000 psig and 40° C., and extracted for 10 minutes with pure $CO_2$. This fraction was collected in methanol in a glass vial, numbered 4 in the figure. Next, depressurization was carried out in a period of less than about 5 minutes in order to disrupt the cells. Next, the extraction parameters were set to: Supercritical $CO_2$ at 3000 psig and extraction temperature 40° C., step extractions with methanol as cosolvent at 0, 5, 10, 20, and 50 vol % (the modifier content of the last fraction was varied as described below), each step being 10 min. Because some void volume remained between the glass beads, the composition of the extraction medium did not change sharply or immediately when modifier flowrate was adjusted to give a new fluid composition. Each sample thus yielded 6 fractions, which were collected in methanol in separate glass vials. The different collection vials are mounted in a carousel, numbered 5 in the figure. The vials are automatically positioned by the SFX 3560 extractor apparatus. While the preceding steps were carried out in a continuous flow mode, cessation of flow to allow static contact time is also contemplated. This procedure may allow a reduction in the amount of extraction solvent required.

Several different assays were used to compare the critical fluid extracts to the butanol extracts and aqueous supernatants.

EXAMPLE 1

Cytotoxicity assay

Microbial extracts were screened for cytotoxicity using the M109 mouse lung carcinoma cell line. The cell line was derived from the M109 tumor grown in vivo in syngeneic BALB/c mice. The cytotoxic activity was determined by incubating the cells with test materials for 48 hours in microtiter plates, and measuring viable cell number using the neutral red staining technique.

To obtain the microbial extracts for this example, organisms were grown up essentially as described above. After fermentation, the broth was split in half, and half was extracted with n-butanol as described above. The cells in the second half of the broth were pelleted by centrifugation and the aqueous supernatant reserved for screening. The cell pellet was dried and extracted with critical fluid as described above, except that the final fraction utilized 100% methanol rather than 50%. The butanol extract, aqueous supernatant, and 6 methanolic fractions from the critical fluid procedure were then screened for cytotoxicity. Results for two organisms tested are shown in Table 2. Positive cytotoxic activity in a particular fraction is indicated by a plus sign, while a minus sign indicates no cytotoxic activity.

TABLE 2

Cytotoxicity Screening Results

| Organism | Medium | H₂O | BuOH | Vol % MeOH in $CO_2$ | | | | | |
|---|---|---|---|---|---|---|---|---|---|
| | | | | 0 | 0 | 5 | 10 | 20 | 100 |
| APH003 | B | – | – | – | – | + | + | – | – |
| APH005 | A | – | – | – | – | + | + | + | + |

Table 2 Notes:
Medium B - Glucose 0.2%, Fish peptone 2%, Yeast extract 0.2%, GP2 sea water.
Medium A - Starch 3%, Glucose 0.2%, Fish peptone 0.2%, Yeast extract 0.2%, GP2 sea water.

EXAMPLE 2

Antimicrobial assay

Microbial extracts were tested for antimicrobial activity by a disk diffusion assay. Diffusion of the the metabolites into the agar creates a zone of growth inhibition around the disk if the organism is susceptible to the antimicrobial metabolite.

Ten to 20 µl amounts of extract or extract fractions were applied to Whatman 3MM filter paper disks 7 mm in diameter. The disks were dried under vacuum overnight to evaporate the solvent. Bioassays were carried out with the target organism *Bacillus subilis*. The target organisms were grown in nutrient broth (Difco), and adjusted to an A600 of 0.1. One hundred µl of the cell suspension was applied to the surface of a nutrient agar plate and spread uniformly with a sterile spreader. After the liquid had absorbed into the agar, the disks were placed on the surface, about 1 cm apart. The plates were incubated at 25°–30° C. for 24–36 hours. Antimicrobial activity was indicated by a zone of inhibition around a disk where bacterial growth was prevented. Because this assay requires diffusion of the active ingredients into the agar, a positive reading shows that the active ingredients are at least partly hydrophilic.

Table 3 shows the results of the antimicrobial assay, with a plus sign indicating positive activity and a minus sign an absence of activity. In addition, positive and negative control disks were utilized. For the negative control, a disk which received only methanol was run in each test. This ensured that all of the methanol had been evaporated and that false positives did not occur. For the positive control, disks containing the antimicrobial gentamycin (10 µg) were used. These disks showed zones of inhibition for all valid experiments.

TABLE 3

Antimicrobial Screening Results

| Organism | Medium | H₂O | BuOH | Vol % MeOH in $CO_2$ | | | | | |
|---|---|---|---|---|---|---|---|---|---|
| | | | | 0 | 0 | 5 | 10 | 20 | 50 |
| APH224 | J | – | – | – | – | + | + | – | – |
| APH238 | K | – | – | + | – | – | – | – | – |
| APH269 | C | – | – | – | – | + | + | + | – |

Table 3 Notes:
Medium J - Glucose 1%, Glycerol 0.5%, Na Acetate 0.5%, Fish peptone 1%, Yeast extract 0.2%, GP2 sea water.
Medium K - Glucose 0.5%, Glycerol 0.5%, Fish peptone 0.2%, Yeast extract 0.2%, GP2 sea water.
Medium C - Glucose 0.2%, Fish peptone 0.2%, Yeast extract 0.2%, GP2 sea water.

EXAMPLE 3

Anti-HIV whole cell assays

The anti-HIV activity of organic solvent and critical fluid extracts was evaluated in an in vitro whole cell cytoprotection assay described by Weislow, et al. (*J Natl. Cancer Inst.* 81:577–586, 1989), using human T cells and the HIV-1 virus. Viable human T cells will survive infection with the HIV-1 virus in the presence of potential antiviral compounds.

For cytoprotection assays, viral antigens were titrated in the selected cell line to determine the minimal dose that would infect and lyse >90% of the cells. This dose was used to determine if any of the test samples prevented cell death. The results were assessed spectrophotometrically by reading optical densities after addition of the tetrazolium reagent (XTT) to determine if the viable cells reduced the pale yellow XTT to an orange formazan product.

Test samples were diluted in the appropriate solvent, and transferred to the test plate. Virus, cells, and RPMI 1640 medium were added to the respective wells, and the plates incubated for 6 days. All wells were examined for cytopathic effects and HIV associated syncytia. By day 3 it was possible to observe protection of HIV infected cells with active compounds. This data was recorded and used to help with the interpretation of results produced by the measurement of formazan production. On day 6, the XTT solution is added to the plates, and cell viability is measured by the visible light absorbance. Data were expressed as a percentage of formazan produced in test wells compared to formazan produced in wells of untreated control cells.

The syncytium-forming assay described by Nara and Fischinger (*Nature* 332:469, 1988) was also used in primary screens and to confirm antiviral activity. In this assay, a single infectious unit of virus infects a single cell and initiates a focal cell change such as syncytium formation. Because a single infectious unit causes a single response, a linear relationship exists between the number of cytopathic effects caused by viral infection and the virus concentration.

The quantitative infectivity syncytium-forming assay was applied to the direct quantitation of fusigenic virus-infected CEM-SS cells. With HIV-1 RF strain the syncytia can be counted usually by day 3. To determine if the test compounds had antiviral activity, the total number of syncytia forming units in the viral control were compared to the count from the test wells. The syncytium assay was also useful to confirm activity observed in the cytoprotection assay. When the plates from the cytoprotection screen were observed microscopically on days 3 to 5, compounds that inhibited cell killing and syncytia formation were selected for confirmation of viral inhibition in this assay. Supernatant fluids can be removed from the wells containing the active compound and titrated for viable virus. The failure of a supernatant fluid to induce syncytia (or reduced numbers of syncytia compared to the viral control) was a rapid and significant second indicator that the compound or extract had anti-HIV activity. For these tests, a positive control utilizing the anti-HIV compound dideoxyinosine was employed. Table 4 shows the results of the anti-HIV screening with a plus sign indicating positive activity and a minus sign indicating a lack of activity. The first organism shows the less frequent case in which activity was found in a butanol extract but not in a critical fluid extract.

TABLE 4

Anti-HIV-1 Screening Results

| Organism | Medium | H₂O | BuOH | \multicolumn{6}{c}{Vol % MeOH in CO₂} |
|---|---|---|---|---|---|---|---|---|---|

| Organism | Medium | H$_2$O | BuOH | 0 | 0 | 5 | 10 | 20 | 30 |
|---|---|---|---|---|---|---|---|---|---|
| APH001 | G | − | + | − | − | − | − | − | − |
| APH001 | E | − | − | − | − | − | + | − | − |
| APH014 | E | − | − | + | − | − | − | + | − |

Table 4 Notes:
Medium G - Glucose 1%, Glycerol 1%, Na acetate 1%, Fish peptone 2%, Yeast extract 0.2%, GP2 sea water.
Medium E - Glucose 1%, Fish peptone 0.2%, Yeast extract 0.2%, GP2 sea water.

The preceding examples have been chosen to demonstrate the the utility of the present invention, and show that in many cases it may provide an advantage over conventional methods. As indicated in Example 3, in less frequent cases activity may be found in the butanol extract or aqueous supernatant, and not in the critical fluid extracts. Clearly, however, the method of this invention may provide access to important chemical species not obtained by more conventional means. Furthermore, the fractionation procedure can be important as activity may be concentrated into specific critical fluid fractions.

The critical fluid disruption process is applicable to both prokaryotic and eukaryotic microorganisms. The present invention will also be useful with other biomass substrates such as plant-, animal- and viral-derived materials.

While the invention has been described in terms of screening for and production of natural therapeutics, it is of potential benefit in any application where fractionation of a substrate containing sequestered materials is desirable. For example, useful chemicals may be discovered for applications in the chemical, petrochemical, environmental, food, cosmetics, or pulp and paper industries.

It is intended that the matter contained in the preceding description be interpreted in an illustrative rather than a limiting sense.

We claim:

1. A method of extracting one or more fractions from a biomass containing one or more cells, comprising the steps of:
   a) contacting said biomass with a first critical fluid, said first critical fluid entering said biomass and solvating one or more compounds;
   b) separating said first critical fluid containing said one or more compounds from said biomass to form a first extraction fraction;
   c) decompressing said biomass to form a disrupted biomass;
   d) forming a second extraction fraction by the following steps:
      i.) contacting said disrupted biomass with a second critical fluid having the same or different solvation properties as said first critical fluid, said second critical fluid entering said disrupted biomass and solvating one or more compounds;
      ii.) separating the second fluid with said one or more compounds from said disrupted biomass to form a second extraction fraction;
   e) forming one or more subsequent extraction fractions by repeating the following steps:
      i.) contacting said disrupted biomass with a subsequent critical fluid having the same or different solvation properties as said first and second critical fluids, said subsequent critical fluid entering said disrupted biomass and solvating one or more compounds;
      ii.) separating the subsequent critical fluid with said one or more compounds from said disrupted biomass to form a subsequent extraction fraction.

2. The method of claim 1 wherein at least one of said first critical fluid, second critical fluid and subsequent critical fluid have different solvation properties from each other through the use of a different modifier concentration.

3. The method of claim 1 in which the different solvation properties of the subsequent critical fluids are obtained through the use of different pressures.

4. The method of claim 1 in which the different solvation properties of the subsequent critical fluids are obtained through the use of different temperatures.

5. The method of claim 1 in which the different solvation properties of the subsequent critical fluids are obtained through the use of a combination of different temperatures, pressures and modifier concentrations.

6. The method of claim 1 in which said biomass contains microbial cells.

7. The method of claim 1 in which said biomass contains microbial cells and fermentation broth.

8. The method of claim 1 in which one of said subsequent extraction fractions is a final extraction fraction in which said subsequent critical fluid is a noncritical fluid.

* * * * *